United States Patent [19]

Maki et al.

[11] Patent Number: 5,817,817
[45] Date of Patent: Oct. 6, 1998

[54] PROCESS FOR THE PRODUCTION OF 2,5-DI(ARYLAMINO)-3,6-DIHYDROTEREPHTHALIC ACID DIALKYL ESTER, AND PROCESS FOR THE PRODUCTION OF QUINACRIDONE FROM SAID ESTER AS INTERMEDIATE

[75] Inventors: Hitoshi Maki; Shigeki Kato; Yoshimi Kikuchi, all of Tokyo, Japan

[73] Assignee: Toyo Ink Manufacturing Co., Ltd., Tokyo, Japan

[21] Appl. No.: 848,179

[22] Filed: Apr. 29, 1997

Related U.S. Application Data

[62] Division of Ser. No. 409,931, Mar. 23, 1995, Pat. No. 5,659,036, which is a division of Ser. No. 266,639, Jun. 28, 1994, abandoned.

[30] Foreign Application Priority Data

Jun. 30, 1993 [JP] Japan ................................. 5-160995

[51] Int. Cl.[6] .................................................. C09B 48/00
[52] U.S. Cl. ................................................. 546/56; 546/49
[58] Field of Search ........................................ 546/49, 56

[56] References Cited

U.S. PATENT DOCUMENTS

| | | | |
|---|---|---|---|
| 2,821,529 | 1/1958 | Struve | 546/49 |
| 2,821,530 | 1/1958 | Struve | 546/57 |
| 2,821,541 | 1/1958 | Struve . | |
| 3,156,719 | 11/1964 | Griswold | 546/56 |
| 3,317,539 | 5/1967 | Jaffe | 546/49 |
| 3,372,184 | 3/1968 | Auster . | |
| 3,674,814 | 7/1972 | Aldridge et al. | 260/396 N |
| 3,738,988 | 6/1973 | Jackson | 546/49 |
| 3,752,817 | 8/1973 | Ehrich | 546/49 |
| 3,873,548 | 3/1975 | Ehrich | 546/49 |
| 4,124,768 | 11/1978 | Kirsch et al. | 546/49 |
| 4,812,568 | 3/1989 | Herzog | 546/49 |
| 4,956,464 | 9/1990 | Bender | 546/49 |
| 4,981,997 | 1/1991 | Schütze et al. | 562/421 |
| 5,286,863 | 2/1994 | Babler | 546/49 |
| 5,491,235 | 2/1996 | Campos et al. | 546/56 |
| 5,502,192 | 3/1996 | Ganci | 546/49 |
| 5,591,258 | 1/1997 | Urban | 546/49 |
| 5,610,306 | 3/1997 | Maki et al. | 546/49 |
| 5,616,779 | 4/1997 | Arndt | 546/49 |

FOREIGN PATENT DOCUMENTS

| | | |
|---|---|---|
| 2102222 | 7/1971 | Germany . |
| 2222177 | 11/1972 | Germany . |
| 4119100 | 4/1992 | Germany . |
| 36-13833 | 8/1957 | Japan . |
| 36-11630 | 7/1961 | Japan . |
| 44-3216 | 2/1969 | Japan . |
| 45-16340 | 6/1970 | Japan . |
| 52-51400 | 4/1977 | Japan . |
| 52-43497 | 10/1977 | Japan . |
| 52-134630 | 11/1977 | Japan . |
| 53-26823 | 3/1978 | Japan . |
| 54-119532 | 9/1979 | Japan . |
| 57-57749 | 4/1982 | Japan . |
| WO94/10249 | 5/1994 | WIPO . |

OTHER PUBLICATIONS

Toyo Ink, Patent Abstracts of Japan, vol. 16 No. 496(C–995) (5539) 14 Oct. 1992 JP-A-04183753.
Kawasaki Chem. Database WPI Week 7506, Derwent Pub. Ltd., London GB AN75–09914SW JP-A-49108036 14 Oct. 1974.

*Primary Examiner*—Donald G. Daus
*Attorney, Agent, or Firm*—Wenderoth, Lind & Ponack L.L.P.

[57] ABSTRACT

A process for producing 2,5-di(arylamino)-3,6-dihydroterephthalic acid dialkyl ester having a high purity from 1,4-cyclohexanedione-2,5-di(carboxylic acid alkyl ester) at high yields for a short period of time; a process for producing quinacridone of which the byproduct content is small, from the above 2,5-di(arylamino)-3,6-dihydroterephthalic acid dialkyl ester; and a process for producing quinacridone of which the particle diameter is adjusted as desired, from the above 2,5-di(arylamino)-3,6-dihydroterephthalic acid dialkyl ester without adding a step of forming a pigment.

4 Claims, No Drawings

PROCESS FOR THE PRODUCTION OF 2,5-DI(ARYLAMINO)-3,6-DIHYDROTEREPHTHALIC ACID DIALKYL ESTER, AND PROCESS FOR THE PRODUCTION OF QUINACRIDONE FROM SAID ESTER AS INTERMEDIATE

This is a divisional application of Ser. No. 08/409,931 filed Mar. 23, 1995, now U.S. Pat. No. 5,659,036, which is a divisional application of now abandoned Ser. No. 08/266,639, filed Jun. 28, 1994, abandoned.

FIELD OF THE INVENTION

The present invention relates to a process for producing a 2,5-di(arylamino)-3,6-dihydroterephthalic acid dialkyl ester having a high purity as an important intermediate for the production of a quinacridone pigment, in high yields without purification, and a process for the production of a quinacridone from the 2,5-di(arylamino)-3,6-dihydroterephthalic acid dialkyl ester.

PRIOR ART OF THE INVENTION

It is known that a 2,5-di(arylamino)-3,6-dihydroterephthalic acid dialkyl ester as an intermediate for the production of a quinacridone pigment is obtained by polycondensation-reacting 1,4-cyclohexanedione-2,5-di(carboxylic acid alkyl ester) with an aromatic amino compound in such amounts that the molar ratio of the 1,4-cyclohexanedione-2,5-di(carboxylic acid alkyl ester) to aromatic amino compound is ½.

The purity of the above intermediate is a critical factor for producing a quinacridone having a high purity in high yields and for the subsequent formation of the pigment. For producing a quinacridone, there is known a method in which 6,13-dihydroquinacridone is synthesized by allowing 2,5-di(arylamino)-3,6-dihydroterephthalic acid dialkyl ester to undergo a intramolecular-alcohol-elimination, ring-closing reaction at a high temperature and oxidized to obtain a quinacridone, or a method in which 2,5-di(arylamino)-3,6-dihydroterephthalic acid is synthesized by saponifying an ester portion and oxidizing a formed central ring and further allowed to react with a ring-closing agent to obtain a quinacridone. In both the above methods, the purity of the 2,5-di(arylamino)-3,6-dihydroterephthalic acid dialkyl ester affects the properties of a quinacridone as an end product when no purification procedures are carried out in the course of carrying out the above methods.

Therefore, studies have been made to improve the purity of the above 2,5-di(arylamino)-3,6-dihydroterephthalic acid dialkyl ester or the purity of other intermediates. Japanese Patent Publication No. 37-18733 discloses a method in which succinosuccinic acid diester is synthesized from succinic acid ester in a dialkylcarboxylic acid solvent, an arylamino compound such as aniline and an acid catalyst are added to the reaction mixture and the mixture is allowed to react in nitrogen current under atmospheric pressure to obtain a 2,5-di(arylamino)-3,6-dihydroterephthalic acid dialkyl ester. This method requires an additional step in which water is added to the reaction mixture and the resultant mixture is cooled to precipitate a reaction product, since the reaction product is present being dissolved in the solvent. In this method, therefore, a longer period of time is required for the production, and the yield is low, as low as 35 to 85%.

Japanese Patent Publication No. 36-11630 discloses the method in which a reaction mixture is directly used for the next step without precipitating 2,5-di(arylamino)-3,6-dihydroterephthalic acid dialkyl ester from the synthesis solvent. In this method, 1,4-cyclohexanedione-2,5-di(carboxylic acid ethyl ester) is synthesized from succinic acid ethyl ester in the presence of a mixture of biphenyl with a diphenyl ether as a solvent (commercially available in the trade name of "Dowtherm A"), byproducts dissolved in the reaction mixture are removed by washing, then, an excess amount of an aromatic amino compound and a hydrochloric acid salt of an aromatic amino compound of the same kind are added, the intended reaction of the resultant mixture is carried out under reduced pressure, a nitrogen gas is introduced up to atmospheric pressure when the reaction reaches a final point, and the hydrochloric acid of the solvent is neutralized with sodium carbonate. The so-formed 2,5-di(arylamino)-3,6-dihydroterephthalic acid dialkyl ester is completely dissolved in the "Dowtherm A", and an excess amount of aromatic amino compound is hence distilled off under reduced pressure before carrying out the subsequent reaction. In this method, the procedures from the reaction of succinic acid ethyl ester to the production of 6,13-dihydroquinacridone are carried out in one reactor, and the number of production apparatus can be hence decreased. However, the yield of 2,5-di(arylamino)-3,6-dihydroterephthalic acid dialkyl ester is not very high, or 85%, and a large amount of energy and a long period of time are required for distilling off an excess of water and an aromatic amino compound. Further, the filtration, washing and purification are not carried out in the course of the production. It hence cannot be said that impurities have no influence on the end product.

It is made known by JP-A-53-26823 that even a trace amount of a dissolved aromatic amino compound has an extraordinary influence on the yield and purity of 6,13-dihydroquinacridone when the 6,13-dihydroquinacridone is produced from pure 2,5-di(arylamino)-3,6-dihydroterephthalic acid dialkyl ester in the presence of "Dowtherm A". The aromatic amino compound can be separated from "Dowtherm A" to a certain extent by distillation, while it is assumed that the aromatic amino compound cannot be completely separated by distillation due to the solubility of the aromatic amino compound in "Dowtherm A". Therefore, it is not preferred to carry out the procedures from the reaction of succinic acid ethyl ester through the formation of 2,5-di(arylamino)-3,6-dihydroterephthalic acid dialkyl ester to the production of 6,13-dihydroquinacridone in one reactor in the presence of the same solvent.

For overcoming the above defect, JP-A-53-26823 discloses a method in which 1,4-cylcohexanedione-2,5-di(carboxylic acid alkyl ester) and an aromatic amino compound are allowed to undergo a condensation reaction in the presence of an inert gas while the aromatic amino compound is used in an excess amount so that it works as a reactant and a solvent, then, an inert solvent having a high boiling point such as "Dowtherm A" is charged, an excess amount of aromatic amino compound is distilled off under reduced pressure, and a reaction mixture (solution or slurry) containing 2,5-di(arylamino)-3,6-dihydroterephthalic acid dialkyl ester and the inert solvent having a high boiling point such as "Dowtherm A" is fed to exactly the same solvent having a high boiling point which has been heated up to 250° C. or higher thereby to produce 6,13-dihydroquinacridone. However, the defect in that an excess amount of the aromatic amino compound is required to be distilled off still remains to be solved. The above method therefore cannot be said to be industrially advantageous due to the long period of time required for the series of operations and many steps required. Further, when oxidized to a corresponding quinacridone, the 6,13-dihydroquinacridone obtained by the above method hardly gives a quinacridone having a high product quality due to the influence of a trace amount of the above aromatic amino compound.

Further, JP-B-60-16411 discloses a method in which 1,4-cyclohexanedione-2,5-di(carboxylic acid alkyl ester) and an aromatic amino compound are allowed to undergo a condensation reaction in the presence of an aromatic nitro compound having no substituent in the o-position as a solvent or a diluent. This method also seeks to carry out the subsequent reaction without isolating 2,5-di(arylamino)-3, 6-dihydroterephthalic acid dialkyl ester. When 6,13-dihydroquinacridone is produced, not an excess amount of the aromatic amino compound but the presence of the aromatic nitro compound inhibits the formation of the 6,13-dihydroquinacridone, and the above method is hence disadvantageous.

JP-A-62-205163 (corresponding to U.S. Pat. No. 4,812, 568) describes an Example in which a reaction between 1,4-cyclohexanedione-2,5-di(carboxylic acid alkyl ester) and an aromatic amino compound is carried out in a reactor in the presence of methanol as a solvent and glacial acetic acid as a catalyst. Since, however, the reactor is not flushed with an inert gas, 2,5-di(arylamino)terephthalic acid dialkyl ester is inevitably formed, and the reaction requires a long period of time, as long as 6 hours. Further, since glacial acetic acid used as a catalyst forms almost no salt with the aromatic amino compound, it is difficult to separate aromatic amino compound and acetic acid from a solution exhausted after filtration and washing. Moreover, glacial acetic acid is used in an amount of 1.3 mol per mole of 1,4-cyclohexanedione-2,5-di(carboxylic acid alkyl ester) used as a raw material, or the amount of glacial acetic acid used as a catalyst is too large. When the end product is subjected to thin layer chromatography for determining the amount of residual materials, the 2,5-di(arylamino)-3,6-dihydroterephthalic acid dialkyl ester has a purity of only 96 to 98%, and the above method is not industrially efficient.

The intramolecular-alcohol-elimination reaction for forming 6,13-dihydroquinacridone from 2,5-di(arylamino)-3,6-dihydroterephthalic acid dialkyl ester is disclosed, for example, in Japanese Patent Publications Nos. 36-11630 and 44-3216, U.S. Pat. No. 2,821,541, Japanese Patent Publication No. 45-16340, JP-A-52-134630, JP-A-52-51400, JP-A-53-26823, JP-B-55-47626, JP-B-57-57749 and JP-A-62-205163. However, the methods disclosed in Japanese Patent Publications Nos. 36-11630, 44-3216 and 45-16340 and JP-A-52-134630 only give 6,13-dihydroquinacridones having a purity of less than 99%, and show a low conversion, as low as 90%. Byproducts formed in addition to the end product, 6,13-dihydroquinacridone, include 3-alkoxycarbonyl-2-anilino-1,4-dihydro-9-acridanone, 2,5-dianilinoterephthalic acid and 3-carboxyl-2-anilino-1,4-dihydro-9-acridanone, and these are liable to be formed when the alcohol-elimination, ring-closing reaction is carried out in a solvent having a high boiling point.

U.S. Pat. No. 2,821,541 discloses a method in which 2,5-di(arylamino)-3,6-dihydroterephthalic acid dialkyl ester is synthesized in "Dowtherm A" and then subjected to a ring-closing reaction by heating it. In this method, however, not only the yield is low, but also it is necessary to carry out the synthesis of 2,5-di(arylamino)-3,6-dihydroterephthalic acid dialkyl ester while water formed during the synthesis is removed. Thus, the above method is industrially disadvantageous.

Further, in JP-A-53-26823, 2,5-di(arylamino)-3,6-dihydroterephthalic acid dialkyl ester is synthesized in a solvent having a high boiling point such as "Dowtherm A", aromatic amino compound remaining after the synthesis is distilled off under reduced pressure, the resultant product is fed to a preheated solvent having a high boiling point, and the ring-closing reaction is carried out to obtain 6,13-dihydroquinacridone. In principle, however, the aromatic amino compound is not removed by washing or cleaning the 2,5-di(arylamino)-3,6-dihydroterephthalic acid dialkyl ester, and therefore it affects the formation of 6,13-dihydroquinacridone all the same.

Further, JP-B-55-47626 discloses methyl naphthalene, biphenyl and diphenyl oxide as solvents having a high boiling point. However, these give lower yields and purities of the product due to their lower boiling points than that of "Dowtherm A". JP-A-57-57749 discloses benzyl ether as the above solvent, and JP-A-62-205163 discloses dimethyl diphenyl ether as the above solvent. However, these Publications fail to define the purity of 2,5-di(arylamino)-3,6-dihydroterephthalic acid dialkyl ester used and the amount of aromatic amino compound contained therein. Further, the boiling points of the above solvents having a high boiling point are not proper, and the results obtained in these Publications are not satisfactory with regard to the yield, purity and reaction time.

The oxidation of 6,13-dihydroquinacridone is disclosed in Examples of 9 to 15 U.S. Pat. No. 2,821,529, Examples 1 to 6 of UK Patent 909602 and Examples 1 to 11 of UK Patent 911477. Since, however, these Patents give only quinacridone as coarse particles, there is required a step of forming a pigment for use as a coloring material.

The oxidation of 6,13-dihydroquinacridone proceeds as a solid-liquid or solid-gas reaction in which particles form cores and are oxidized, since it has low solubility in organic solvents. In a practical sense, therefore, it is impossible to obtain quinacridone particles having a smaller size than the dihydroquinacridone particles which are to be oxidized. That is, the step of forming a pigment can be omitted only when 6,13-dihydroquinacridone having a proper size for a pigment is oxidized. The 6,13-dihydroquinacridones obtained by the methods disclosed Japanese Patent Publications 36-11630 and 44-3216, JP-A-57-57749, JP-A-62-205163, etc., are of coarse particles having a specific surface area of 10 $m^2/g$ or less, and when these coarse particles are oxidized by any one of the methods disclosed in Japanese Patent Publications Nos. 36-138333, U.S. Pat. No. 3,007,930, JP-A-53-94334, etc., industrially disadvantageously, it is required to add a step of forming a pigment.

The oxidation and saponification of 2,5-di(arylamino)-3,6-dihydroterephthalic acid dialkyl ester into 2,5-di(arylamino)terephthalic acid are disclosed, for example, in JP-A-49-108036 and JP-A-51-598301. However, nothing is specified concerning 2,5-di(arylamino)-3,6-dihydroterephthalic acid dialkyl ester used and the influence of byproducts, and the yield and purity of the formed 2,5-di(arylamino)terephthalic acid and the reaction time are not satisfactory.

Further, the intramolecular-dehydration, ring-closing reaction of 2,5-di(arylamino)terephthalic acid, e.g., a method using polyphosphoric acid or sulfuric acid, is disclosed in Japanese Patent Publications Nos. 36-17826, 37-14928 and 38-21632, JP-A-53-37730 and JP-B-61-21263. A method using a ring-closing agent and a catalyst in the presence of an organic solvent is disclosed in Japanese Patent Publications Nos. 42-5414 and JP-B-56-45434. In the method using polyphosphoric acid or sulfuric acid, however, the form of a crystal varies depending upon the method of precipitating quinacridone after the ring-closing reaction. Further, when polyphosphoric acid is used, it can be recovered only in the form of phosphoric acid when water is included, and for converting the phosphoric acid into polyphosphoric acid, it is required to add phosphorus pentaoxide. As a result, the amount of polyphosphoric acid gradually increases. Therefore, the above method is not industrially advantageous, and further, the yield of quinacridone is not high. Meanwhile, the method using a ring-closing agent and a catalyst in the presence of an organic solvent has an advantage in that the solvent can be recovered, while the yield of quinacridone is not high. Further, both the above ring-closing methods give coarse particles of quinacridone, and industrially disadvantageously, the above methods require a subsequent step of forming a pigment for using the quinacridone as a coloring material.

The present inventors have made diligent studies of optimum reaction conditions for producing 2,5-di(arylamino)-3,6-dihydroterephthalic acid dialkyl ester most suitable for obtaining quinacridone suitable for use as a pigment through the oxidation of 6,13-dihydroquinacridone or through the ring-closing of 2,5-di(arylamino)terephthalic acid, and as a result, have found optimum reaction conditions on the basis of the mixing ratio of 1,4-cyclohexanedione-2,5-di(carboxylic acid alkyl ester), an aromatic amino compound and a catalyst and the kind of the catalyst. Further, it has been found that 6,13-dihydroquinacridone or 2,5-di(arylamino)terephthalic acid suitable for producing a quinacridone pigment can be obtained from 2,5-di(arylamino)-3,6-dihydroterephthalic acid dialkyl ester under certain conditions.

SUMMARY OF THE INVENTION

It is an object of the present invention to provide a process for producing 2,5-di(arylamino)-3,6-dihydroterephthalic acid dialkyl ester having a high purity from 1,4-cyclohexanedione-2,5-di(carboxylic acid alkyl ester) in high yields for a short period of time.

It is another object of the present invention to provide a process for producing quinacridone of which the byproduct content is small, from the above 2,5-di(arylamino)-3,6-dihydroterephthalic acid dialkyl ester.

Further, it is another object of the present invention to provide a process for producing quinacridone of which the particle diameter is adjusted as desired, from the above 2,5-di(arylamino)-3,6-dihydroterephthalic acid dialkyl ester without adding a step of forming a pigment.

According to the present invention, there is provided a process for the production of 2,5-di(arylamino)-3,6-dihydroterephthalic acid dialkyl ester by a condensation reaction between 1,4-cyclohexanedione-2,5-di(carboxylic acid alkyl ester) and an aromatic amino compound of the formula (1),

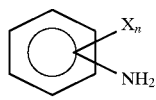

(1)

wherein X is F, Cl, Br, I, —OH, —NO$_2$, —CF$_3$, an alkyl group having 1 to 4 carbon atoms, a substituted alkyl group having 1 to 4 carbon atoms, an alkoxy group having 1 to 4 carbon atoms, a substituted alkoxy group having 1 to 4 carbon atoms, a phenyl group, a cyclohexyl group, a phenoxy group, —COOH, a —COO—

$C_1$–$C_4$alkyl group, —SO$_3$H, a phenylamino group, a benzenamino group, —N(CH$_3$)$_2$, —SO$_2$HN$_2$, —SO$_2$N(CH$_3$)$_2$, a pyridino group, —CONH$_2$ or —CON(CH$_3$)$_2$, and n is an integer of 0 to 4, provided that a hydrogen atom is positioned on at least one ortho-position relative to the NH$_2$, the amount of the aromatic amino compound of the formula (1) being 2.0 to 4.0 mol per mole of the 1,4-cyclohexanedione-2,5-di(carboxylic acid alkyl ester), the said polycondensation reaction being carried out in the presence, as a catalyst, of hydrochloric acid or sulfuric acid in an amount of 0.04 to 1.10 mol per mole of the 1,4-cyclohexanedione-2,5-di(carboxylic acid alkyl ester) and in the presence, as a solvent, of a lower alcohol having 1 to 4 carbon atoms, in an oxygen-free atmosphere at a reaction temperature between 80° C. and 130° C.

Further, according to the present invention, there is provided a process for producing quinacridone, which comprises heating the above-obtained 2,5-di(arylamino)-3,6-dihydroterephthalic acid dialkyl ester in an organic solvent up to a temperature between 250° C. and 350° C. in an oxygen-free atmosphere, thereby proceeding with an intramolecular-alcohol-elimination reaction to convert the 2,5-di(arylamino)-3,6-dihydroterephthalic acid dialkyl ester to 6,13-dihydroquinacridone, and oxidizing the 6,13-dihydroquinacridone.

Further, according to the present invention, there is provided a process for producing quinacridone, which comprises oxidizing and saponifying the above-obtained 2,5-di(arylamino)-3,6-dihydroterephthalic acid dialkyl ester to covert the 2,5-di(arylamino)-3,6-dihydroterephthalic acid dialkyl ester to 2,5-di(arylamino)terephthalic acid, and then heating the 2,5-di(arylamino)terephthalic acid up to a temperature between 100° C. and 180° C. in a sulfuric acid or polyphosphoric acid to carry out intramolecular dehydration and ring-closing thereof.

Further, according to the present invention, there is provided a process for producing quinacridone, which comprises oxidizing and saponifying the above-obtained 2,5-di(arylamino)-3,6-dihydroterephthalic acid dialkyl ester to covert the 2,5-di(arylamino)-3,6-dihydroterephthalic acid dialkyl ester to 2,5-di(arylamino)terephthalic acid, mixing the 2,5-di(arylamino)terephthalic acid with a ring-closing agent in an organic solvent slightly miscible with water in the presence of a catalyst, and heating the resultant mixture up to a temperature between 150° C. and 210° C. to carry out intramolecular dehydration and ring closing of the 2,5-di(arylamino)terephthalic acid.

DETAILED DESCRIPTION OF THE INVENTION

The alkyl of the 1,4-cyclohexanedione-2,5-di(carboxylic acid alkyl ester) used in the present invention is a lower alkyl group having 1 to 4 carbon atoms or a substituted alkyl group having 1 to 4 carbon atoms. Specific examples of the alkyl include methyl, ethyl, isopropyl, n-butyl, iso-butyl, sec-butyl and tert-butyl. This alkyl group is dissociated as an alcohol when the intramolecular-alcohol elimination reaction takes place. The number of carbon atoms of this alkyl group is hence perferably the same as the number of carbon atoms of a solvent used, and the purity thereof is preferably at least 99%.

The solvent used in the present invention is a lower alcohol having 1 to 4 carbon atoms, and examples thereof include methanol, ethanol, n-propanol, iso-propanol, n-butanol and iso-butanol. When these solvents are used, only a very small amount of 1,4-cyclohexanedione-2,5-di(carboxylic acid alkyl ester) as a raw material is dissolved therein at room temperature. However, at the reaction temperature employed in the present invention, 1,4-cyclohexanedione-2,5-di(carboxylic acid alkyl ester) can be fully dissolved in the solvent of which the weight is 7 to 14 times as large as the weight of the raw material. Further, in the temperature range of from room temperature to the reaction temperature, only a very small amount of the formed 2,5-di(arylamino)-3,6-dihydroterephthalic acid dialkyl ester is dissolved therein.

The aromatic amino compound used in the present invention is a compound of the formula (1) in which a hydrogen atom is positioned in at least one ortho-position relative to the amino group substituted on the aromatic ring. The substituent (X in the formula (1)) which can be substituted on the aromatic ring for hydrogen includes F, Cl, Br, I, —OH, —$NO_2$, —$CF_3$, an alkyl group having 1 to 4 carbon atoms, a substituted alkyl group having 1 to 4 carbon atoms, an alkoxy group having 1 to 4 carbon atoms, a substituted alkoxy group having 1 to 4 carbon atoms, a phenyl group, a cyclohexyl group, a phenoxy group, —COOH, a —COO—$C_1$–$C_4$alkyl group, —$SO_3H$, a phenylamino group, a benzamino group, —$N(CH_3)_2$, —$SO_2HN_2$, —$SO_2N(CH_3)_2$, a pyridino group, —$CONH_2$ and —$CON(CH_3)_2$. The number (n in the formula (1)) of the above substituents may be introduced onto the aromatic ring is 0 to 4, and a plurality of these substituents may be the same or different.

The catalyst used in the present invention refers to a generally used acid such as hydrochloric acid or sulfuric acid. The smaller the amount of water dissolved therein is, the better, since the main reaction proceeds in a dehydration-condensation reaction.

The amount of the aromatic amino compound per mole of the 1,4-cyclohexanedione-2,5-di(carboxylic acid alkyl ester) is 2.0 to 4.0 mol, and the amount of the catalyst per mole of the 1,4-cyclohexanedione-2,5-di(carboxylic acid alkyl ester) is 0.04 to 1.10 mol. Preferably, the difference obtained by deducting the molar amount of the catalyst from the molar amount of the aromatic amino compound is 2.3 to 2.9 when these molar amounts are calculated on an assumption that the molar amount of the 1,4-cyclohexanedione-2,5-di(carboxylic acid alkyl ester) is 1. That is, the amount of the aromatic amino compound is considered to be a positive factor which improves the purity and yield of 2,5-di(arylamino)-3,6-dihydroterephthalic acid to be formed when this amount is increased, and the amount of the catalyst is considered to be a negative factor which has an adverse effect on the above purity and yield when this amount is increased. Therefore, when the difference obtained by offsetting these positive and negative factors is in a proper range, the product having the highest purity can be obtained at a high yield.

Oxygen is another negative factor. When oxygen is present in the reaction system, 1,4-cyclohexanedione-2,5-di(carboxylic acid alkyl ester) is completely dissolved in the solvent when the 1,4-cyclohexanedione-2,5-di(carboxylic acid alkyl ester) reaches the reaction temperature, and the 1,4-cyclohexanedione-2,5-di(carboxylic acid alkyl ester) is oxidized by dehydrogenation sooner than it undergoes a dehydration condensation reaction with the aromatic amino compound. Or, when the aromatic amino compound undergoes a condensation with one molecule of 1,4-cyclohexanedione-2,5-di(carboxylic acid alkyl ester), the condensate is oxidized by dehydrogenation. Or, the formed 2,5-di(arylamino)-3,6-dihydroterephthalic acid dialkyl ester is oxidized by dehydrogenation. In any event, a byproduct other than the intended product is formed. The formation of these byproducts can be prevented by flushing the pressure reactor with an inert gas such as nitrogen, carbon dioxide or argon gas before the reactants charged in the pressure reactor are stirred under heat.

1,4-Cyclohexanedione-2,5-di(carboxylic acid alkyl ester), the aromatic amino compound, the catalyst and the solvent in the above-described amounts are charged into a pressure reactor up to 70% of the total volume of the pressure reactor or less, and the pressure reactor is closed. Then, the pressure in the pressure reactor is increased and decreased repeatedly with an inert gas to fully replace oxygen with the inert gas, and thereafter, an inert gas is introduced up to a pressure of 0 to 5 kg/$cm^2$ at a gage pressure. The reactants are temperature-increased up to the predetermined reaction temperature, and allowed to react, with stirring at a circumferential speed of 20 to 120 m/minute. The reaction proceeds by about 95% for a reaction time of 90 minutes, and thereafter it gradually proceeds. Therefore, the reaction takes about 3 to 5 hours. After the reaction, the reaction mixture is immediately cooled to room temperature, and an alkali in a minimum amount necessary to neutralize the acid used as the catalyst is added in the form of an aqueous solution. Then, the reaction mixture is stirred for a while, and the inert gas increasing the pressure in the pressure reactor is released, the product is filtered, and the filtrate is washed with a wash liquid until the filtrate becomes transparent. The wash liquid is the same lower alcohol as the alcohol used as the solvent, and it is heated up to about 60° C. in advance. In the present invention, the synthesis of 2,5-di(arylamino)-3,6-dihydroterephthalic acid dialkyl ester proceeds at high yields. When the 2,5-di(arylamino)-3,6-dihydroterephthalic acid dialkyl ester formed according to the process of the present invention is measured for purity by liquid chromatography and IR, it is found to have a remarkable purity. This product can be processed into an intermediate for the intended quinacridone by the subsequent reaction even if it contains methanol or is in the state of an aqueous paste.

The 2,5-di(arylamino)-3,6-dihydroterephthalic acid dialkyl ester obtained according to the above process of the present invention is mixed, for example, with a heating medium commercially available in the trade name of "Dowtherm A" which is a mixture biphenyl and diphenyl ether, or with any one of alkylnapthalene, N-methylpyrrolidone, dibenzyl ether and t-amyl alcohol, and the mixture is heated up to 200° to 350° C. under atmospheric pressure or elevated pressure, whereby the alkyl group and arylamino group of the ester portion of the 2,5-di(arylamino)-3,6-dihydroterephthalic acid dialkyl ester undergo intramolecular-alcohol-elimination and the 2,5-di(arylamino)-3,6-dihydroterephthalic acid dialkyl ester is converted to a corresponding 6,13-dihydroquinacridone which is substituted as required.

The corresponding 6,13-dihydroquinacridone substituted as required is preferably obtained by mixing the above 2,5-di(arylamino)-3,6-dihydroterephthalic acid dialkyl ester with dimethylnaphthalene isomer mixture of which the weight is 3 to 15 times as large as that of the 2,5-di(arylamino)-3,6-dihydroterephthalic acid dialkyl ester, either heating the mixture to a temperature not higher than 150° C. or bringing the mixture into a non-heated state, and gradually adding the mixture to a dimethylnaphthalene isomer mixture of which the weight is 3 to 15 times as large as that of the mixture and which is heated to 200° to 350°

C. in advance, under atmospheric pressure or elevated pressure in an oxygen-free atmosphere.

In the above reaction for obtaining 6,13-dihydroquinacridone, oxygen works as a negative factor as is already explained. Therefore, 6,13-dihydroquinacridone having a high purity can be obtained by carrying out the above reaction in an oxygen-free state.

The 6,13-dihydroquinacridone obtained by the above process of the present invention can be converted to a corresponding quinacridone, for example, by oxidizing the 6,13-dihydroquinacridone with an oxidizing agent such as sodium m-nitrobenzenesulfonate, nitrobenzene, nitronaphthalene, nitrobenzenesulfonic acid, nitrobenzenecarboxylic acid, nitrophenol, oxygen or air, in the presence of a mixed solvent of methanol, ethanol, acetone, ethylene glycol or glycol ether with water, in the presence of an alkali, at a high temperature, optionally under elevated pressure, and optionally in the presence of a dispersing agent and a reaction promoter. The oxidation is carried out, for example, with air in the presence of a dispersing agent, preferably an anionic dispersing agent such as a condensate from aromatic sulfonic acid and formaldehyde, and the quinacridone is formed as coarse particles. For using these particles of quinacridone as a coloring material, it is required to carry out a so-called pigmentation step of converting the coarse particles to fine particles.

The oxidation of 6,13-dihydroquinacridone is a solid-liquid reaction or a solid-gas reaction in which particles of 6,13-dihydroquinacridone forms cores and are oxidized since the 6,13-dihydroquinacridone has low solubility in organic solvents. It is hence practically impossible to obtain quinacridone particles having a smaller size than that of the dihydroquinacridone to be oxidized. In other words, the pigmentation step can be omitted only when 6,13-dihydroquinacridone particles having a size smaller than the size suitable as a pigment are oxidized.

However, the 6,13-dihydroquinacridone obtained by the above process of the present invention gives an unconventional quinacridone substituted as required, which does not require the pigmentation step, by a method in which the 6,13-dihydroquinacridone is converted to a salt in a solution containing 40 to 96% by weight of a lower alcohol having 1 to 4 carbon atoms, 4 to 30% by weight of sodium hydroxide or potassium hydroxide and 0 to 30% by weight of water, either mineral acid or water and an alcohol are added so that the resultant mixture has a concentration of an alkali which amount is equal to, or lower than, a stoichiometric amount and that the salt is hydrolyzed, thereby to obtain 6,13-dihydroquinacridone having a specific surface area of at least 20 $m^2/g$ and having a uniform size, and the so-obtained 6,13-dihydroquinacridone is oxidation-treated with an oxidizing agent selected from nitrobenzenesulfonic acids, anthraquinonesulfonic acids, sodium polysulfide and oxygen in a $C_1$–$C_4$ lower alcohol solution containing 1.5 to 20% by weight of sodium hydroxide and 2 to 40% by weight of water.

In the above method, the purity of 6,13-dihydroquinacridone is critical. Almost no publications which have been available describe the purity of 6,13-dihydroquinacridone to be oxidized. When a byproduct formed during the dehydration condensation reaction between 1,4-cyclohexanedione-2,5-di(carboxylic acid alkyl ester) and the aromatic amino compound remains in the 2,5-di(arylamino)-3,6-dihydroterephthalic acid dialkyl ester, the byproduct inhibits the conversion of the 2,5-di(arylamino)-3,6-dihydroterephthlalic acid dialkyl ester to 6,13-dihydroquinacridone and causes the formation of a new byproduct. As a result, the 6,13-dihydroquinacridone has a low purity. When 6,13-dihydroquinacridone having a byproduct content of 1% or more is converted to a salt and oxidized in an alcohol-alkali solvent, the growth of particles and the oxidation are greatly prevented, and no desirable particle form is obtained. When such 6,13-dihydroquinacridone is oxidized according to the above process of the present invention, the oxidation rate is very low, and only a quinacridone having a low purity is obtained. This byproduct has a low solubility in organic solvents as described already, and it is hence difficult to remove the byproduct. It is therefore important to control the reaction so that the above byproduct is not formed.

In contrast, 6,13-dihydroquinacridone containing no byproduct and having a high purity easily forms a salt in an alcohol solution in the presence of an alkali. That is because >C=O groups bond to Na and K as is the case with quinacridone, it is clear that an alkali is required in an amount of at least 2 mol (at least a stoichiometric amount) per mole of 6,13-dihydroquinacridone. The formed salt of 6,13-dihydroquinacridone is hydrolyzed by decreasing the amount of an alkali to less than the stoichiometric amount. Particles of 6,13-dihydroquinacridone formed by the above hydrolysis are obtained as fine particles which have a specific surface area of at least 20 $m^2/g$ and are easily oxidized, whereby an excellent quinacridone pigment can be obtained.

The above process of the present invention is the most preferably carried out as follows. That is, 6,13-dihydroquinacridone having a high purity is charged into a proper reactor having a stirrer and a reflux device together with a lower alcohol having 1 to 4 carbon atoms and a necessary amount of a water-soluble alkali. When the mixture is stirred, the 6,13-dihydroquinacridone and the alkali form a salt. The solvent (lower alcohol) includes methanol, ethanol, n-propanol, iso-propanol, n-butanol and iso-butanol, while methanol is preferred. The water-soluble alkali includes potassium hydroxide and sodium hydroxide, while sodium hydroxide is preferred in view of easiness in forming the salt, economic performance and easiness in controlling particles. For improving the solubility of the alkali in the mixture, it is preferred to add a small amount of water (preferably the same amount as that of the alkali). The amount of the solvent (alcohol+water-soluble alkali+water) is 3 to 30 times, preferably 5 to 15 times, as large as the weight of the 6,13-dihydroquinacridone. The solvent contains 40 to 96% by weight of the alcohol, 4 to 30% by weight of the water-soluble alkali and 0 to 30% by weight of water, preferably contains 70 to 88% by weight of the alcohol, 6 to 20% by weight of the water-soluble alkali and 6 to 20% by weight of water. The salt formation proceeds at a relatively high rate, while the salt is easily formed when the alkali concentration is high. When the 6,13-dihydroquinacridone is formed into a salt, it becomes a large crystal having a size of about 30 $\mu$m. After the salt is formed, a mineral acid such as sulfuric acid or hydrochloric acid, water or alcohol is added to the solution containing the above crystal, whereby the crystal is hydrolyzed to give fine 6,13-dihydroquinacridone particles having a specific surface area of 20 to 40 $m^2/g$.

For the oxidation, the solvent solution containing the above hydrolyzed 6,13-dihydroquinacridone is adjusted to an alcohol solution containing 1.5 to 20% by weight of the water-soluble alkali and 2 to 40% by weight, preferably 2 to 30% by weight, of water. When the solvent solution has an alkali concentration less than a salt-forming concentration, the oxidation may be initiated without adjusting the alkali concentration. However, when the solvent solution has an alkali concentration higher than the salt-forming concentration, the 6,13-dihydroquinacridone forms a salt again, and no intended pure quinacridone substituted as required is obtained. The oxidizing agent is selected from nitrobenzenesulfonic acids, anthraquinonesulfonic acids, sodium polysulfide and oxygen. Above all, sodium m-nitrobenzenesulfonate is preferred, since the oxidation proceeds moderately. A strong oxidizing agent such as oxygen is liable to promote the oxidation and form quinacridone-quinone. When the alkali concentration is adjusted to 1.5 to 20% by weight for the oxidation, there are obtained quinacridone particles which are uniform and have a specific surface area of 10 to 40 $m^2/g$.

The purity of 6,13-dihydroquinacridone (unsubstituted) is measured, for example, by the following method.

Dihydroquinacridone content (wt %)=0.205×(Abs241−0.527×Abs598−2.93×B)/A×100

B=Abs440−0.047×Abs598

Abs241=absorbance at 241 nm

Abs440=absorbance at 440 nm

Abs598=absorbance at 598 nm

A sample is weighed in an exact amount of 4 mg (exactness of 0.01 mg, this weight is referred to as A (mg)), and dissolved in special-grade sulfuric acid in a 100-ml measuring flask to prepare a constant volume. The sample was measured for absorbance at 24° to 26° C. with a 1 cm thick quartz cell, and sulfuric acid is used as a reference liquid.

The 2,5-di(arylamino)-3,6-dihydroterephthalic acid dialkyl ester produced according to the present invention can be converted to a corresponding 2,5-di(arylamino) terephthalic acid by treating it in a mixed solvent of a solvent with water in the presence of an oxidizing agent and an alkali, at a high temperature, optionally under elevated pressure and optionally in the presence of a dispersing agent and a reaction promoter. The above oxidizing agent includes sodium m-nitrobenzenesulfonate, nitrobenzene, nitronaphthalene, nitrobenzenesulfonic acid and nitrophenol. The above solvent includes methanol, ethanol, acetone, ethylene glycol and glycol ether.

Further, the 2,5-di(arylamino)terephthalic acid obtained by the above process of the present invention can be converted to a corresponding quinacridone by heating the 2,5-di(arylamino)terephthalic acid up to 100° to 180° C. while mixing it with polyphosphoric acid or ultraphosphoric acid of which the weight is 5 to 20 times as large as that of the 2,5-di(arylamino)terephthalic acid. In this process, the 2,5-di(arylamino)terephthalic acid undergoes an intramolecular-dehydration, ring-closing reaction to be converted to a corresponding quinacridone. Or, the 2,5-di (arylamino)terephthalic acid can be converted to a corresponding quinacridone by a method in which the 2,5-di (arylamino)terephthalic acid is mixed with a ring-closing agent and an acid catalyst or an organic catalyst in an organic solvent slightly miscible with water and the mixture is heated up to 150° to 210° C., whereby the 2,5-di(arylamino) terephthalic acid undergoes an intramolecular-dehydration, ring-closing reaction to be converted to a corresponding quinacridone. The above ring-closing agent includes nitrobenzene, nitronaphthalene, aniline, phosgene, benzoyl chloride and ethylene glycol. The above acid catalyst includes hydrochloric acid and acetic acid. The above organic catalyst includes quinoline.

When the 6,13-dihydroquinacridone is oxidized or when the 2,5-di(arylamino)terephthalic acid is allowed to undergo an intramolecular-dehydration, ring-closing reaction, 1 to 20% by weight of a quinacridone pigment derivative such as a basic quinacridone pigment derivative disclosed in JP-A-2-123168 (corresponding to U.S. Pat. No. 5,368,641) or an acidic or neutral quinacridone pigment derivative of the following formula (2) may be added, whereby a quinacridone pigment having an adjusted desirable crystal state can be obtained and the quinacridone pigment can be imparted with advantageous surface properties and practically advantageous properties.

wherein Q is an unsubstituted quinacridone residue or a quinacridone residue substituted with a halogen atom, an alkyl group having 1 to 4 carbon atoms, an alkoxy group having 1 to 4 carbon atoms, $H_2N—CO—$ or a $C_1-C_4$ alkyl-NH—CO— group, each of $X_1$ and $X_2$ is independently a hydrogen atom, a halogen atom (when $X_1$ and $X_2$ are hydrogen atoms and halogen atoms, each of i and j is an integer of at least 2, or one of the substituents of the following formulae (3), and each of i and j is independently an integer of 1 to 4),

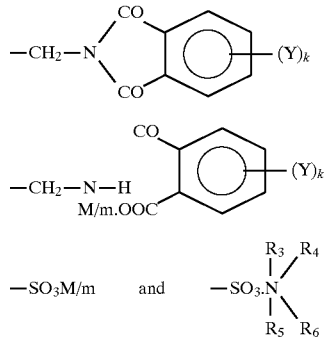

wherein Y is a hydrogen atom, a halogen atom, $—NO_2$ or $—SO_3H$, M is a hydrogen atom, a calcium atom, a barium atom, a strontium atom or an aluminum atom, each of $R_3$, $R_4$, $R_5$ and $R_6$ is a hydrogen atom (excluding a case where all of $R_3$, $R_4$, $R_5$ and $R_6$ are hydrogen atoms) or an alkyl group having 1 to 30 carbon atoms, k is an integer of 1 to 4, and m is a valence of M.

Further, when the 6,13-dihydroquinacridone is oxidized or when the 2,5-di(arylamino)terephthalic acid is allowed to undergo an intramolecular-dehydration, ring-closing reaction, a quinacridone having a desired crystal form may be added, whereby a quinacridone having a desired crystal form can be obtained.

The following quinacridones can be synthesized according to the present invention.

Quinacridone, 2,9-dichloroquinacridone, 3,10-dichloroquinacridone, 4,11-dichloroquinacridone, 2,3,9,10-tetrachloroquinacridone, 2,4,9,11-tetrachloroquinacridone, 2,9-difluoroquinacridone, 2,9-dibromoquinacridone, 2,9-dimethylquinacridone, 3,10-dimethylquinacridone, 4,11-dimethylquinacridone, 2,4,9,11-tetramethylquinacridone, 2,9-di(tert-butyl)quinacridone, 2,9-dihydroxylquinacridone, 2,9-di(trifluoromethyl)quinacridone, 2,9-dimethoxyquinacridone, 2,9-diethoxyquinacridone, 2,4,9,11-tetramethoxyquinacridone, 2,9-dicarboxylquinacridone, 2,9-dichlorohexylquinacridone, 2,9-diphenylquinacridone, 2,9-di(dimethylamino)quinacridone, 2,9-di(dimethylaminosulfo)quinacridone, 2,9-di(dimethylaminocarbonyl)quinacridone, 3,10-dinitroquinacridone, 2,9-dimethyl-4,11-dichloroquinacridone, 2,9-dimethyl-4,11-dicarboxyquinacridone, and 2,9-dipyridinoquinacridone.

The quinacridone obtained in the present invention is remarkably excellent in weatherability and masking properties, and it can be used in a paste, a flash color, a print coloring material, a lacquer, a peroxide curing varnish and a polyurethane varnish. The quinacridone obtained in the present invention can be incorporated into synthetic and natural polymers. These polymers include thermoplastic resins such as polyvinyl chloride, polystyrene, polyethylene, polyester, phenolplast, aminoplast and rubber. Further, the quinacridone obtained in the present invention can be incorporated into natural, recycled and synthetic fiber materials, and it can be also incorporated into organic and inorganic pigments.

A mixture containing the quinacridone obtained in the present invention as a coloring component may be any one of a solid, an elastomer, a paste and a viscous material. An aqueous paste is obtained, for example, by adding a wetting agent or a dispersing agent to the pigment and stirring the mixture in water, or by adding the pigment to a dispersing agent and dispersing or kneading the mixture in the presence of water and optionally an organic solvent or an oil. This paste can be used for producing a flash color, a print coloring material, an aqueous coating composition, a plastic dispersion and a spinning liquid. The quinacridone obtained in the present invention can be incorporated into water, an organic solvent, a non-drying oil, a drying oil, a lacquer, a varnish, a plastic and rubber by stirring, roll-stirring, kneading or milling.

The present invention will be explained hereinafter with reference to Examples, in which "part" stands for "part by weight" and "%" stands for "% by weight".

EXAMPLE 1

A 1-liter autoclave of pressure glass was charged with 45.60 parts (0.2 mol) of 1,4-cyclohexanedione-2,5-di(carboxylic acid methyl ester) well dried, 46.57 parts (0.5 mol) of aniline, 500 parts of methanol and 4.65 parts (0.045 mol) of 35% hydrochloric acid, and the autoclave was tightly closed. Then, oxygen in the autoclave was fully replaced with nitrogen gas, and the pressure in the autoclave was set at a gage pressure of 0 kg/cm$^2$. While the mixture was vigorously stirred, the temperature in the autoclave was increased from room temperature to 100° C. over 15 minutes, and then the mixture was allowed to react for 3 hours. The highest pressure in the autoclave during the reaction was 3.8 kg/cm$^2$. The reaction mixture was cooled to 30° C. or lower, and then, the pressure was released to a level of atmospheric pressure. 18 Parts of a 10% NaOH aqueous solution was charged, and after the mixture was stirred for 10 minutes, the reaction product was filtered. The resultant cake was fully washed with methanol having a temperature of 60° C. The yield of the formed 2,5-dianilino-3,6-dihydroterephthalic acid dimethyl ester was 75.07 parts, which was 99.3% of the theoretical yield. Further, the purity thereof was 99.5%.

Comparative Example 1

A 1-liter flask having a condenser and a nitrogen-introducing tube was charged with 45.60 parts (0.2 mol) of 1,4-cyclohexanedione-2,5-di(carboxylic acid methyl ester), 46.57 parts (0.5 mol) of aniline, 500 parts of methanol and 4.65 parts (0.045 mol) of 35% hydrochloric acid, and oxygen in the flask was fully replaced with nitrogen gas. Then, while the mixture was vigorously stirred, the temperature in the flask was increased from room temperature to boiling point of 65° C. over 15 minutes, and the mixture was allowed to react for 3 hours. The reaction mixture was cooled to 30° C. or less, and then, 18 parts of a 10% NaOH aqueous solution was charged. Then, the mixture was stirred for 10 minutes, the reaction product was filtered, and fully washed with methanol having a temperature of 60° C. The yield of the formed 2,5-dianilino-3,6-dihydroterephthalic acid dimethyl ester was 72.46 parts, which was 95.8% of the theoretical yield. Further, the purity thereof was 94.3%.

Comparative Example 2

Comparative Example 1 was repeated except that the amount of aniline was changed to 39.49 parts (0.424 mol) and that the amount of 35% hydrochloric acid was changed to 6.96 parts (0.067 mol). The yield of the formed 2,5-dianilino-3,6-dihydroterephthalic acid dimethyl ester was 66.54 parts (88.02% of the theoretical yield). Further, the purity thereof was 97.4%.

EXAMPLE 2

Example 1 was repeated except that the amount of aniline was changed to 51.41 parts (0.552 mol) and that the amount of 35% hydrochloric acid was changed to 1.25 parts (0.012 mol). The yield of the formed 2,5-dianilino-3,6-dihydroterephthalic acid dimethyl ester was 75.22 parts (99.50% of the theoretical yield). Further, the purity thereof was 99.4%.

EXAMPLE 3

Example 1 was repeated except that the aniline was replaced with 69.56 parts (0.545 mol) of p-chloroaniline, to give 88.24 parts (98.7% of the theoretical yield) of 2,5-di(p-chloroanilino)- 3,6-dihydroterephthalic acid dimethyl ester. The purity thereof was 99.5%.

Comparative Example 3

Comparative Example 1 was repeated except that the aniline was replaced with 69.56 parts (0.545 mol) of p-chloroaniline, to give 84.39 parts (94.4% of the theoretical yield) of 2,5-di(p-chloroanilino)-3,6-dihydroterephthalic acid dimethyl ester. The purity thereof was 95.1%.

EXAMPLE 4

Example 1 was repeated except that the aniline was replaced with 58.39 parts (0.545 mol) of p-toluidine, to give 80.31 parts (98.9% of the theoretical yield) of 2,5-di(p-toluidino)-3,6-dihydroterephthalic acid dimethyl ester. The purity thereof was 99.6%.

Comparative Example 4

Comparative Example 1 was repeated except that the aniline was replaced with 58.39 parts (0.545 mol) of p-toluidine, to give 76.41 parts (94.1% of the theoretical yield) of 2,5-di(p-toluidino)-3,6-dihydroterephthalic acid dimethyl ester. The purity thereof was 94.6%.

EXAMPLE 5

Example 1 was repeated except that the 1,4-cyclohexanedione-2,5-di(carboxylic acid methyl ester) was replaced with 51.2 parts (0.2 mol) of 1,4-cyclohexanedione-2,5-di(carboxylic acid ethyl ester) and that the methanol was replaced with 500 parts of ethanol, to give 80.14 parts (98.7% of the theoretical yield) of 2,5-dianilino-3,6-dihydroterephthalic acid diethyl ester. The purity thereof was 99.4%.

EXAMPLE 6

Example 1 was repeated except that the 35% hydrochloric acid was replaced with 4.50 parts (0.045 mol) of 98% sulfuric acid, to give 73.71 parts (97.5% of the theoretical yield) of 2,5-dianilino-3,6-dihydroterephthalic acid dimethyl ester. The purity thereof was 99.0%.

EXAMPLE 7

Example 1 was repeated except that the methanol was replaced with 500 parts of n-propanol and that the reaction temperature was set at 120° C., to give 74.16 parts (98.1% of the theoretical yield) of 2,5-dianilino-3,6-dihydroterephthalic acid dimethyl ester. The purity thereof was 99.1%.

EXAMPLE 8

Example 1 was repeated except that the methanol was replaced with 500 parts of iso-butanol and that the reaction temperature was set at 120° C., to give 74.39 parts (98.4% of the theoretical yield) of 2,5-dianilino-3,6-dihydroterephthalic acid dimethyl ester. The purity thereof was 99.2%.

Comparative Example 5

Example 1 was repeated except that the methanol was replaced with 500 parts of 2-methyl-1-pentanol and that the reaction was carried out at a boiling point of 136° C. under atmospheric pressure, to give 71.74 parts (94.9% of the theoretical yield) of 2,5-dianilino-3,6-dihydroterephthalic acid dimethyl ester. The purity thereof was 97.6%.

EXAMPLE 9

30 Parts of the 2,5-dianilino-3,6-dihydroterephthalic acid dimethyl ester obtained in Example 1 and 150 parts of a dimethylnaphthalene isomer mixture were charged into a 200-ml flask having an outlet valve in the bottom, and the mixture was heated up to 120° to 170° C. with stirring under nitrogen gas atmosphere. Then, the resultant hot mixture was added to 150 parts of the same dimethylnaphthalene isomer mixture as that used above in a 500 ml-flask over 20 to 40 minutes, which dimethylnaphthalene isomer mixture was stirred under nitrogen gas atmosphere and maintained at 280° C. Then, the mixture was further maintained at 280° to 283° C. (reflux) for 30 minutes.

On adding the hot mixture of 2,5-dianilino-3,6-dihydroterephthalic acid dimethyl ester with the dimethylnaphthalene isomer mixture, which hot mixture had a temperature of 120° to 170° C., to the dimethylnaphthalene isomer mixture, the reaction for the formation of 6,13-dihydroquinacridone was initiated while methanol was generated, and the generation of methanol almost finished immediately after the reflux at 283° C. was initiated.

The reaction mixture was cooled to 100° C., and then the nitrogen gas atmosphere was removed. The reaction mixture was filtered, washed with 500 ml of hot methanol and dried to give 24.47 parts (98.2 % of the theoretical yield) of 6,13-dihydroquinacridone. The 6,13-dihydroquinacridone was measured for a purity by IR and absorbance to show at least 99%.

Comparative Example 6

Example 9 was repeated except that the 2,5-dianilino-3,6-dihydroterephthalic acid dimethyl ester used in Example 9 was replaced with 30 parts of the 2,5-dianilino-3,6-dihydroterephthalic acid dimethyl ester obtained in Comparative Example 1, to give 23.5 parts (94.5% of the theoretical yield) of 6,13-dihydroquinacridone. The 6,13-dihydroquinacridone was measured for a purity by IR and absorbance to show 96.8%.

EXAMPLE 10

Example 9 was repeated except that the dimethylnaphthalene isomer mixture used in Example 9 was replaced with a mixed solvent commercially available in the trade name of "Dowtherm A", to give 24.3 parts (97.5% of the theoretical yield) of 6,13-dihydroquinacridone. The 6,13-dihydroquinacridone was measured for a purity by IR and absorbance to show at least 99%.

Comparative Example 7

Example 10 was repeated except that the 2,5-dianilino-3,6-dihydroterephthalic acid dimethyl ester used in Example 10 was replaced with 30 parts of the 2,5-dianilino-3,6-dihydroterephthalic acid dimethyl ester obtained in Comparative Example 1, to give 22.2 parts (89.1% of the theoretical yield) of 6,13-dihydroquinacridone. The 6,13-dihydroquinacridone was measured for a purity by IR and absorbance to show 96.2%.

EXAMPLE 11

79 Parts of methanol and 12 parts of a 50% NaOH aqeuous solution were fully stirred in a flask of stainless steel. 10 Parts of the 6,13-dihydroquinacridone obtained in Example 9 and 10 parts of sodium m-nitrobenzenesulfonate were gradually added, and the mixture was refluxed at 70° to 75° C. for 3 to 5 hours. The mixture was cooled until it had a temperature of 40° C. or lower, and the mixture was filtered. The resultant cake was washed with hot water until the wash water was colorless and transparent, and dried, to give 9.78 parts (98.4% of the theoretical yield) of an unsubstituted quinacridone. The quinacridone was measured for a purity by IR and absorbance to show 99.2% of quinacridone and 0.8% of 6,13-dihydroquinacridone. The quinacridone had a specific surface area of 22.8 m$^2$/g.

Comparative Example 8

Example 11 was repeated except that the 6,13-dihydroquinacridone used in Example 11 was replaced with the 6,13-dihydroquinacridone obtained in Comparative Example 6, to give 9.69 parts (97.5% of the theoretical yield) of an unsubstituted quinacridone. The quinacridone was measured for a purity by IR and absorbance to show 96.7% of quinacridone and 2.9% of 6,13-dihydroquinacridone. Further, the so-obtained quinacridone was formed into a coating composition, the coating composition was compared with a coating composition from the quinacridone obtained in Example 11 to show a color difference of ΔE=2.4 and that the coating composition from the quinacridone in this Example was yellowish and dull. The quinacridone had a specific surface area of 35.4 m$^2$/g.

EXAMPLE 12

Example 11 was repeated except that the sodium m-nitrobenzenesulfonate was replaced with sodium anthraquinone-β-sulfonate, to give 9.69 parts (97.5% of the theoretical yield) of an unsubstituted quinacridone. The quinacridone was measured for a purity by IR and absorbance to show 98.9% of quinacridone and 0.7% of 6,13-dihydroquinacridone. Further, the so-obtained quinacridone was formed into a coating composition, the coating composition was compared with a coating composition from the quinacridone obtained in Example 11 to show a color difference of ΔE=0.4 and that the coating composition from the quinacridone in this Example was bluish but clear. The quinacridone had a specific surface area of 24.1 m²/g.

EXAMPLE 13

8.9 Parts of 2,5-di(p-chloroanilino)-3,6-dihydroterephthalic acid dimethyl ester, 50 parts of ethanol, 5.37 parts of KOH, 24.35 parts of water and 6 parts of sodium m-nitrobenzenesulfonate were charged into a 200-ml flask of stainless steel, and refluxed with stirring for 10 hours. When the suspension changed to a black solution, ethanol was steam-distilled, and the reaction mixture was filtered to remove a solid. The remaining solution was heated up to 80° C. with stirring, and after 35 parts of a 10% hydrochloric acid aqueous solution was dropwise added, the mixture was maintained for 1 hour. Then, the mixture was filtered, washed with hot water and dried to give 8.21 parts (98.4% of the theoretical yield) of 2,5-di(p-chloroanilino) terephthalic acid.

Comparative Example 9

Example 13 was repeated except that the 2,5-di(p-chloroanilino)-3,6-dihydroterephthalic acid dimethyl ester used in Example 13 was replaced with 8.94 parts of the 2,5-di(p-chloroanilino)-3,6-dihydroterephthalic acid dimethyl ester obtained in Comparative Example 3, to give 7.72 parts (92.6% of the theoretical yield) of 2,5-di(p-chloroanilino)terephthalic acid.

EXAMPLE 14

Example 13 was repeated except that the sodium m-nitrobenzenesulfonate was replaced with air and that the reaction was carried out while the air was blown into a solution in the flask at 20 ml/minute during the reaction, to give 8.02 parts (96.2% of the theoretical yield) of 2,5-di(p-chloroanilino)terephthalic acid.

EXAMPLE 15

7.51 Parts of 2,5-di(p-chloroanilino)terephthalic acid obtained in Example 13, 79 parts of nitrobenzene, 6 parts of benzoyl chloride and 1.65 parts of quinoline were charged into a 200-ml flask of stainless steel, and maintained at 200° C. for 5 hours. When the mixture was temperature-increased up to about 180° C., hydrochloric acid gas was generated and the intramolecular-dehydration reaction was initiated. The reaction mixture was cooled to 110° C., and then 2.27 parts of 30% sodium hydroxide was dropwise added to decompose an excess of benzoyl chloride. Then, the reaction mixture was filtered while it was hot, washed with methanol, washed with water and dried to give 6.37 parts (92.8% of the theoretical yield) of 2,9-dichloroquinacridone.

Comparative Example 10

Example 15 was repeated except that the 2,5-di(p-chloroanilino)terephthalic acid used in Example 15 was replaced with 7.51 parts of the 2,5-di(p-chloroanilino) terephthalic acid obtained in Comparative Example 9, to give 5.95 parts (86.7% of the theoretical yield) of 2,9-dichloroquinacridone.

EXAMPLE 16

10 Parts of the 6,13-dihydroquinacridone obtained in Example 9 and 80 parts of methanol were charged into a 200-ml flask having a refluxer, and stirred. 12 Parts of a 50% NaOH aqueous solution was added, and the mixture was stirred at 40° C. for 30 minutes to form a salt. 26 Parts of 10% sulfuric acid was added dropwise to hydrolyze the salt, and the reaction mixture was refluxed under heat for 1 hour. 10 Parts of sodium m-nitrobenzenesulfonate was added, and immediately therafter, 3 parts of a 50%. NaOH aqeuous solution was added. Then, the mixture was refluxed for 4 hours to give 9.82 parts (98.8% of the theoretical yield) of an unsubstituted quinacridone having an excellent particle diameter as a pigment.

EXAMPLE 17

10 Parts of the 6,13-dihydroquinacridone obtained in Example 9 and 80 parts of methanol were charged into a 200-ml flask having a refluxer, and stirred. 12 Parts of a 50% NaOH aqueous solution was added, and the mixture was stirred at 40° C. for 30 minutes to form a salt. 26 Parts of 10% sulfuric acid was added dropwise to hydrolyze the salt, and the reaction mixture was refluxed under heat for 1 hour. 10 Parts of sodium m-nitrobenzenesulfonate was added, and immediately therafter, 50 parts of a 50% NaOH aqeuous solution was added. Then, the mixture was refluxed for 4 hours to give 9.88 parts (99.4% of the theoretical yield) of an unsubstituted quinacridone having an excellent particle diameter as a pigment.

EXAMPLE 18

10 Parts of the 6,13-dihydroquinacridone obtained in Example 9 and 80 parts of methanol were charged into a 200-ml flask having a refluxer, and stirred. 12 Parts of a 50% NaOH aqueous solution was added, and the mixture was stirred at 40° C. for 30 minutes to form a salt. 40 Parts of 10% sulfuric acid was added dropwise to hydrolyze the salt, and the reaction mixture was refluxed under for 1 hour. 10 Parts of sodium m-nitrobenzenesulfonate was added, and the mixture was refluxed for 4 hours to give 9.76 parts (98.2% of the theoretical yield) of an unsubstituted quinacridone having an excellent particle diameter as a pigment.

Comparative Example 11

10 Parts of the 6,13-dihydroquinacridone obtained in Example 9 and 80 parts of methanol were charged into a 200-ml flask having a refluxer, and stirred. 12 Parts of a 50% NaOH aqueous solution was added, and the mixture was stirred at 40° C. for 30 minutes to form a salt. 40 Parts of 10% sulfuric acid was added dropwise to hydrolyze the salt, and the reaction mixture was refluxed under heat for 1 hour. 10 Parts of sodium m-nitrobenzenesulfonate was added, and the mixture was refluxed for 4 hours to give 9.41 parts (94.7% of the theoretical yield) of an unsubstituted quinacridone. The quinacridone was measured for a purity by IR and absorbance to show 91.2% of quinacridone and 8.8% of 6,13-dihydroquinacridone.

EXAMPLE 19

Example 1 was repeated except that the aniline used in Example 1 was replaced with 93.74 parts (0.545 mol) of p-bromoaniline, to give 96.59 parts (90.1% of the theoretical yield) of 2,5-di(p-bromoanilino)-3,6-dihydroterephthalic acid dimethyl ester. The purity thereof was 98.0%.

EXAMPLE 20

Example 1 was repeated except that the aniline used in Example 1 was replaced with 2,4-dichloroaniline, to give 2,5-di(2,4-dichloroanilino)-3,6-dihydroterephthalic acid dimethyl ester. The purity thereof was 98.0%.

EXAMPLE 21

Example 1 was repeated except that the aniline used in Example 1 was replaced with 2-chloro-4-methylaniline, to give 2,5-di(2-chloro-4-methylanilino)-3,6-dihydroterephthalic acid dimethyl ester. The purity thereof was 98.4%.

EXAMPLE 22

Example 1 was repeated except that the aniline used in Example 1 was replaced with p-phenylaniline, to give 2,5-di(p-phenylanilino)-3,6-dihydroterephthalic acid dimethyl ester. The purity thereof was 97.3%.

EXAMPLE 23

Example 1 was repeated except that the aniline used in Example 1 was replaced with 4-trifluoromethylaniline, to give 2,5-di(4-trifluoromethylanilino)-3,6-dihydroterephthalic acid dimethyl ester. The purity thereof was 97.8%.

EXAMPLE 24

Example 1 was repeated except that the aniline used in Example 1 was replaced with p-carboxylaniline, to give 2,5-di(p-carboxylanilino)-3,6-dihydroterephthalic acid dimethyl ester. The purity thereof was 98.1%.

EXAMPLE 25

Example 1 was repeated except that the aniline used in Example 1 was replaced with 2,3,4,5-tetrachloroaniline, to give 2,5-di(2,3,4,5-tetrachloroanilino)-3,6-dihydroterephthalic acid dimethyl ester. The purity thereof was 94.2%.

EXAMPLE 26

Example 1 was repeated except that the aniline used in Example 1 was replaced with p-sulfoaniline, to give 2,5-di(p-sulfoanilino)-3,6-dihydroterephthalic acid dimethyl ester. The purity thereof was 97.8%.

EXAMPLE 27

Example 1 was repeated except that the aniline used in Example 1 was replaced with p-dimethylaminocarbonylaniline, to give 2,5-di(p-dimethylaminocarbonylanilino)-3,6-dihydroterephthalic acid dimethyl ester. The purity thereof was 94.8%.

EXAMPLE 28

Example 1 was repeated except that the aniline used in Example 1 was replaced with p-dimethylaminoaniline, to give 2,5-di(p-dimethylaminoanilino)-3,6-dihydroterephthalic acid dimethyl ester. The purity thereof was 95.2%.

EXAMPLE 29

Example 13 was repeated except that the 2,5-di(p-chloroanilino)-3,6-dihydroterephthalic acid dimethyl ester used in Example 13 was replaced with 7.56 parts of 2,5-dianilino-3,6-dihydroterephthalic acid dimethyl ester, to give 6.88 parts (98.9% of the theoretical yield) of 2,5-dianilinoterephthalic acid dimethyl ester.

EXAMPLE 30

A 200-ml flask was charged with 6.96 parts of the 2,5-dianilinoterephthalic acid obtained in Example 29 and 70 parts of sulfuric acid having a concentration of 98%, and while the mixture was stirred, the mixture was maintained at 160° C. for 5 hours. Then, the mixture was cooled to 80° C. or lower, and 50 parts of water was gradually added over 4 hours. Then, the mixture was poured into 500 parts of ice-containing water at one stroke, and the mixture was filtered, washed with water and dried to give 5.83 parts (93.5% of the theoretical yield) of an unsubstituted quinacridone.

In the process for producing 2,5-di(arylamino)-3,6-dihydroterephthalic acid dialkyl ester, provided by the present invention, 1,4-cyclohexanedione-2,5-di(carboxylic acid alkyl ester) and the aromatic amino compound are condensation-reacted in a completely dissolved and uniform state by heating a solvent in which 1,4-cyclohexanedione-2,5-di(carboxylic acid alkyl ester) is not dissolved at room temperature and at a boiling temperature, the 1,4-cyclohexanedione-2,5-di(carboxylic acid alkyl ester) and the aromatic amino compound up to a temperature higher than the boiling point in a pressure reactor, whereby the degree of completeness of the reaction is improved and a product having a high purity can be obtained.

Further, the solubility of the product, 2,5-di(arylamino)-3,6-dihydroterephthalic acid dialkyl ester, obtained by the process of the present invention in a lower alcohol having 1 to 4 carbon atoms such as methanol and ethanol is much lower than the solubility of the reactant, 1,4-cyclohexanedione-2,5-di(carboxylic acid alkyl ester) at a boiling point and at the reaction temperature employed in the present invention, and the 2,5-di(arylamino)-3,6-dihydroterephthalic acid dialkyl ester hence easily precipitates in the above lower alcohol. Further, impurities and the unreacted reactant have properties of being easily dissolved in the above lower alcohol. Therefore, the 2,5-di(arylamino)-3,6-dihydroterephthalic acid dialkyl ester can be easily isolated by filtration, and the amount of the solvent for washing the product can be decreased.

The 2,5-di(arylamino)-3,6-dihydroterephthalic acid dialkyl ester obtained by the process of the present invention has a remarkably high purity, and therefore, 6,13-dihydroquinacridone and 2,5-di(arylamino)terephthalic acid having a high purity can be obtained at high yields in the subsequent processes for the production thereof. Further, the corresponding quinacridone having a high purity can be also obtained at high yields by the subsequent reaction.

Quinacridones obtained by prior art techniques have a defect in that since the particles thereof are coarse or very fine aggregates, they require a pigmentation step, while quinacridones substituted as required, obtained in the present invention, easily permits the crystal transition and particle control by a series of steps.

What is claimed is:

1. A process for producing quinacridone which comprises
   (1) producing 2,5-di(arylamino)-3,6-dihydroterephthalic acid dialkyl ester by a condensation reaction between 1,4-cyclohexanedione-2,5-di(carboxylic acid alkyl ester) and an aromatic amino compound of the formula (1),

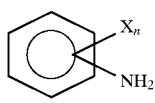 (1)

wherein X is F, Cl, Br, I, —OH, —NO$_2$, —CF$_3$, an alkyl group having 1 to 4 carbon atoms, an alkoxy group having 1 to 4 carbon atoms, a phenyl group, a cyclohexyl group, a phenoxy group, —COOH, a —COO—C$_1$–C$_4$ alkyl group, —SO$_3$H, a phenylamino group, a benzamino group, —N(CH$_3$)$_2$, —SO$_2$HN$_2$, —SO$_2$N(CH$_3$)$_2$, a pyridino group, —CONH$_2$ or —CON(CH$_3$)$_2$, and n is an integer of 0 to 4, provided that a hydrogen atom is positioned in at least one ortho-position relative to the NH$_2$, the amount of the aromatic amino group of the formula (1) being 2.0 to 4.0 mol per mole of the 1,4-cyclohexanedione-2,5-di(carboxylic acid alkyl ester), the said condensation reaction being carried out in the presence, as a catalyst, of hydrochloric acid or sulfuric acid in an amount of 0.04 to 1.10 mol per mole of the 1,4-cyclohexanedione-2,5-di(carboxylic acid alkyl ester) and in the presence, as a solvent, of a lower alcohol having 1 to 4 carbon atoms, in an oxygen-free atmosphere at a reaction temperature between 80° C. and 130° C., after which the 2,5-di(arylamino)-3,6-dihydroterephthalic acid dialkyl ester is isolated, (2) oxidizing the 2,5-di(arylamino)-3,6-dihydroterephthalic acid dialkyl ester in a solution of 1.5 to 20% by weight of a water-soluble alkali and 2 to 40% by weight of water in a lower alcohol having 1 to 4 carbon atoms to convert the 2,5-di(arylamino)-3,6-dihydroterephthalic acid dialkyl ester to 2,5-di(arylamino)terephthalic acid, which is isolated, and (3) carrying out intramolecular dehydration and ring-closing thereof.

2. A process according to claim 1, wherein the oxidizing is carried out in the presence of at least one member selected from the group consisting of nitrobenzenesulfonic acid, anthraquinonesulfonic acid and sodium polysulfide.

3. A process according to claim 1, wherein the intramolecular dehydration and ring-closing is carried out by heating the 2,5-di(arylamino)terephthalic acid up to a temperature of between 100° and 180° C. in a sulfuric acid or polyphosphoric acid.

4. A process according to claim 1, wherein the intramolecular dehydration and ring-closing is carried out by mixing the 2,5-di(arylamino)terephthalic acid in an organic solvent slightly miscible with water in the presence of a catalyst, and heating the resultant mixture up to a temperature between 150° and 210° C.

* * * * *